United States Patent [19]

Welter et al.

[11] Patent Number: 4,910,313

[45] Date of Patent: Mar. 20, 1990

[54] DISELENOBIS BENZOIC ACID AMIDES OF PRIMARY HETEROCYCLIC AMINES, PROCESS FOR PRODUCING THE SAME AND PROCESS FOR THE TREATMENT OF CERTAIN DISEASES IN HUMANS

[75] Inventors: André Welter, Pulheim; Axel Roemer, Hürth-Gleuel; Sigurd Leyck; Michael J. Parnham, both of Pulheim, all of Fed. Rep. of Germany

[73] Assignee: Nattermann & CIE GmbH, Cologne, Fed. Rep. of Germany

[21] Appl. No.: 82,438

[22] Filed: Aug. 6, 1987

[30] Foreign Application Priority Data

Aug. 6, 1987 [DE] Fed. Rep. of Germany ....... 3626554

[51] Int. Cl.$^4$ .................... C07F 5/00; C07D 401/12
[52] U.S. Cl. .................... 546/265; 548/185; 548/192; 548/195; 548/204; 548/243; 548/245; 548/246; 548/247; 549/59; 549/60; 549/435; 549/473
[58] Field of Search ............ 546/265; 549/59, 60, 549/435, 473; 548/185, 192, 195, 204, 243, 245, 246, 247

[56] References Cited

U.S. PATENT DOCUMENTS

| | | | |
|---|---|---|---|
| 4,352,799 | 10/1982 | Renson et al. | 514/183 |
| 4,418,069 | 11/1983 | Welter et al. | 514/359 |
| 4,550,168 | 10/1985 | Welter et al. | 546/270 |
| 4,618,669 | 10/1986 | Dereu et al. | 530/331 |

FOREIGN PATENT DOCUMENTS 3027074  2/1982  Fed. Rep. of Germany ...... 548/108

*Primary Examiner*—Alan L. Rotman
*Attorney, Agent, or Firm*—Pearne, Gordon, McCoy & Granger

[57] ABSTRACT

The present invention is related to new diselenobis benzoic acid amides of primary heterocyclic amines of the general formula I

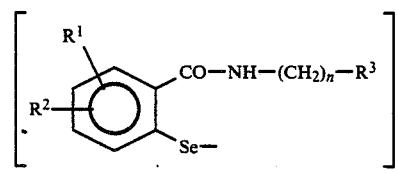

process for producing the same and process for treating certain diseases in human beings by administration of the same to the humans suffering from such diseases.

1 Claim, No Drawings

DISELENOBIS BENZOIC ACID AMIDES OF PRIMARY HETEROCYCLIC AMINES, PROCESS FOR PRODUCING THE SAME AND PROCESS FOR THE TREATMENT OF CERTAIN DISEASES IN HUMANS

The present invention is related to new diselenobis benzoic acid amides of primary heterocyclic amines which are characterized by valuable pharmacological properties. The invention is further related to processes for producing these compounds and to processes for the treatment of certain diseases in human beings, in particular in the treatment of diseases which are caused by cell damage due to the increased formation of active oxygen metabolites such as liver damages, heart infarctions, infections, psoriasis or damages by radiation.

The compounds according to the present invention correspond to the general formula I

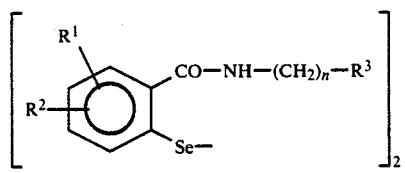

wherein $R^1$ and $R^2$, which may be equal or different from another, represent members selected from the group consisting of hydrogen, halogen, $C_{1-4}$-alkyl, $C_{1-4}$-alkoxy, trifluoromethyl, nitro and, both together, methylenedioxy, n is zero or a numeral ranging from 1 to 4 and $R^3$ is a member selected from the group consisting of the saturated or unsaturated heterocyclic residues with one or two heteroatoms in the cyclic nucleus selected from the group of nitrogen, sulphur and oxygen, said residues being unsubstituted and said residues being substituted onces or twice, equally or in different manner, by halogen, $C_{1-2}$-alkyl, $C_{1-2}$-alkoxy, nitro or hydroxy.

Preferred are those compounds where $R^1$ and $R^2$, which may be equal or different from each other, represent hydrogen, fluorine, chlorine, methyl, methoxy, nitro or, both together, methylenedioxy and n is zero or a numeral from 1 to 4 while $R^3$ is a saturated or unsaturated heterocyclic residue comprising one or two heteroatoms in the cyclic nucleus selected from the group nitrogen, sulphur and oxygen and which are selected from the group of the pyridines, thiazoles, thiophenes, piperidines, pyrrolidines, furanes, isoxazoles and morpholines, said heterocyclic residue being unsubstituted or substituted once or twice in equal manner or different from each other, by chlorine, methyl, methoxy, nitro or hydroxy.

Compounds according to the invention are for instance:

2,2-Diselenobis-(N-2-pyridyl-benzamide)
2,2-Diselenobis-(N-3-pyridyl-benzamide)
2,2-Diselenobis-(N-4-pyridyl-benzamide)
2,2-Diselenobis-[N-2-pyridyl-(4-fluorobenzamide)]
2,2-Diselenobis-[N-2-pyridyl-(4-chlorobenzamide)]
2,2-Diselenobis-[N-2-pyridyl-(4-methylbenzamide)]
2,2-Diselenobis-[N-2-pyridyl-(4-methoxybenzamide)]
2,2-Diselenobis-[N-2-pyridyl-(5-chlorobenzamide)]
2,2-Diselenobis-[N-2-pyridyl-(5-nitrobenzamide)]
2,2-Diselenobis-[N-2-pyridyl-(3-methoxybenzamide)]
2,2-Diselenobis-[N-2-pyridyl-(3,4-methylendioxybenzamide)]
2,2-Diselenobis-[N-(2-chloro-3-pyridyl)-benzamide]
2,2-Diselenobis-[N-(3-hydroxy-2-pyridyl)-benzamide]
2,2-Diselenobis-[N-(6-methoxy-3-pyridyl)-benzamide]
2,2-Diselenobis-[N-(3-nitro-2-pyridyl)-benzamide]
2,2-Diselenobis-[N-(3-methyl-2-pyridyl)-benzamide]
2,2-Diselenobis-[N-(5-methyl-2-pyridyl)-benzamide]
2,2-Diselenobis-[N-(3,5-dichloro-2-pyridyl)-benzamide]
2,2-Diselenobix-[N-(4,6-dimethyl-2-pyridyl)-benzamide]
2,2-Diselenobis-(N-2-thiazolyl-benzamide)
2,2-Diselenobis-[N-(4-methyl-2-thiazolyl)-benzamide]
2,2-Diselenobis-[N-(5-nitro-2-thiazolyl)-benzamide]
2,2-Diselenobis-(N-2-pyridylmethyl-benzamide)
2,2-Diselenobis-(N-3-pyridylmethyl-benzamide)
2,2-Diselenobis-(N-4-pyridylmethyl-benzamide)
2,2-Diselenobis-[N-2-(2-pyridyl)-ethyl-benzamide]
2,2-Diselenobis-(N-2-thienyl-benzamide)
2,2-Diselenobis-(N-2-piperidinoethyl-benzamide)
2,2-Diselenobis-(N-3-piperidinopropyl-benzamide)
2,2-Diselenobis-(N-3-pyrrolidinopropyl-benzamide)
2,2-Diselenobis-(N-furfuryl-benzamide)
2,2-Diselenoibis-[N-2-(2-furyl)-ethyl-benzamide]
2,2-Diselenobis-[N-3-(2-furyl)-propyl-benzamide]
2,2-Diselenobis-[N-4-(2-furyl)-butyl-benzamide]
2,2-Diselenobis-[N-2-(2-(2-tetrahydrofuryl)-ethyl-benzamide]
2,2-Diselenobis-(N-3-isoxazolyl-benzamide)
2,2-Diselenobis-[N-3-(5-methylisoxazolyl)-benzamide]
2,2-Diselenobis-(N-2-morpholinoethyl-benzamide)
2,2-Diselenobis-(N-3-morpholinopropyl-benzamide).

The compounds according to the invention show properties similar to glutathion-peroxidase and therefore can substitute for this enzyme and similar to the reaction of this enzyme together with a mercaptan may prohibit and avoid the damaging activity of active oxygen metabolites.

Glutathion(GSH-peroxidase (Px) which is dependent upon the presence of the element selenium or selenium comprising compounds, catalyses the reduction of $H_2O_2$ and organic hydroperoxides.

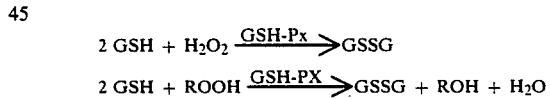

The selenium containing enzyme protects the cells against peroxydation and therefore has an important share in the modulation of arachidonic acid metabolism (C. C. Reddy, E. J. Massaro, Fundam. and Appl. Toxicology (3), 9–10 (1983, pgs. 431–436 and L. Flohé in Free Radicals in Biology, vol. V, edited by W. A. Pryor 1982 Academic Press, pgs. 223–254).

Glutathion-peroxidase plays an important role in all those diseases yielding into a cell damage of the affected tissue and finally yielding into a necrosis because of increased formation of active oxygen metabolites in the form of peroxides (f.i. lipid peroxides and hydrogen peroxide). This so-called "oxidative stress" is for instance observed in liver diseases—induced by inflammatory or autoimmunologic reactions, by alcohol or by drugs, but also in other diseases such as for instance heart infarction. It is known that after a heart infarction leukocytes immigrate into the damaged tissue and that the dying of cell tissue is connected with an increased formation of the above mentioned active oxygen metabolites. This finally yields into an increased decomposition of tissue.

In such cases, the naturally existing protective system against such damage consisting of different enzymes decomposing peroxides and active oxygen, is overstrained. Enzymes for this purpose are for instance superoxiddismutase, katalase, and in particular the glutathione-redox-system with its enzyme component glutathione-peroxidase. This last mentioned enzyme is of particular importance because it may detoxicate tissue from organic peroxides as well as hydrogen peroxide. It is known that this enzyme system is most important for the correct functioning of the liver (Wendel et al.: Biochemical Pharmacology, vol. 31, p. 3601 (1982); Remmer: Deutsches Ärzteblatt-Ärztliche Mitteilungen 79, brochure 26, p. 42 (1982)). The extent of an experimentally produced liver damage is dependent just from this enzyme system, i.e. from the content of glutathione in the liver, on the one side, and from the activity of the enzyme glutathione-peroxidase, on the other side. During a general inflammation this protective mechanism of the liver is extensively reduced (Bragt et al., Agents and Actions, Supp. 17, p. 214 (1980)). Thus, the liver endures a strongly increased "oxidative stress".

The reactive oxygen metabolites are a very important factor as mediators of inflammations. They obviously are an important factor both in leucotaxis, the permeability of blood vessels, in damage of connective tissue in immuncomplex/complement-induced effects as well as in damages occuring in repeated intrusion into ischiemic areas (L. Flohé et al., in The Pharmacology of Inflammation, ed. I.; L. Bonta et al., Handbook of Inflammation, vol. 5, Elsevier, Amsterdam, in preparation).

Damages occuring after ionising radiation are also caused by the formation of radicals and active oxygen metabolites.

Thus, one possibility for chemical cytoprotection is the improvement of the activity of the glutathione/-glutathione-peroxydase-system (H. Rink in: "Glutathione", Proceedings of the 16th Conference of the German Society of Biological chemistry 1973, edited by Flohé, Benöhr, Sies, Walter and Wendel, p. 206).

The measurement of glutathionperoxydase-like activity is effected by the method of A. Wendel (A. Wendel, Methods in Enzymology, vol. 77, pgs. 325-333 (1981)). In this test is determined the conversion of the co-substrate nicotinamide-adenin-dinucleotide-phosphate. The reducing agent in this reaction is glutathione. Surprisingly, it has been found that the compounds of formula I of the present invention produce a glutathione-peroxydase-like activity.

Glutathione-peroxydase-like activity

In in vitro experiments there was tested the catalysis of the degradation of peroxidase. It has been determined that the compounds of the present invention are capable to substitute glutathione-peroxydase.

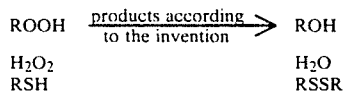

| ROOH | products according to the invention | ROH |
| H₂O₂ | | H₂O |
| RSH | | RSSR |

The catalytic activity is expressed as the amount of glutathione-peroxydase. As reference product is used the recently described product Ebselen=2-phenyl-1,2-benzisoselenazol-3(2H)-one (A. Wendel, M. Fansel, H. Safayhi, G. Tiegs, R. Otter, Biochem. Pharmac. 33, 3241, 1984). The activity of Ebselen is considered as 100% and the activity of the compounds according to the present invention are related to that of Ebselen.

Ebselen has been tested in a concentration of 30 μmole and dimethylformamide (DMF) has been used as solubilizer. The diselenides according to the invention have been tested in a concentration of 15 μmole using DMF as solubilizer, since there are present two atoms of selenium per mole in the diselenides of the invention.

| | Catalytic activity, % |
|---|---|
| Ebselen | 100 |
| 2,/2-diselenobis-[N-3-(5-methyl-isoxazolyl)-benzamide] | 25 |
| 2,/diselenobis-(N-3-pyridyl-benzamide) | 105 |
| 2,/diselenobis-(N-3-pyridylmethyl-benzamide) | 68 |
| 2,/diselenobis-(N-furfuryl-benzamide) | 82 |
| 2,/diselenobis-(N-2-thienyl-benzamide) | 61 |

The compounds of formula I according to the invention are produced in that benzisoselenazolones of the general formula II, wherein $R^1$, $R^2$, $R^3$ and n have the same meaning as in formula I, are reacted with equimolar amounts of a mercaptane such as ethylmercaptane in a suitable organic solvent at room temperature to yield the intermediary compounds of formula III, as shown in the following equation:

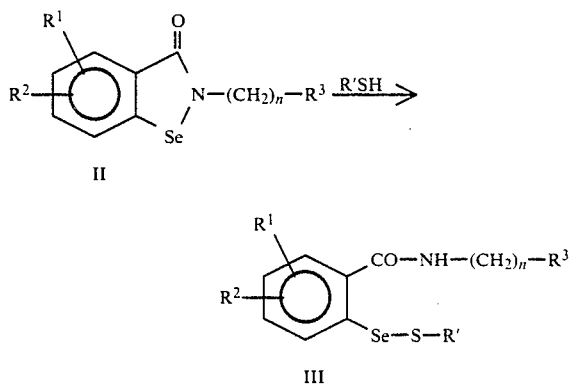

The compounds of formula III at the addition of amines such as methyl amine are readily converted into the compounds of formula I according to the invention as follows from the following equation:

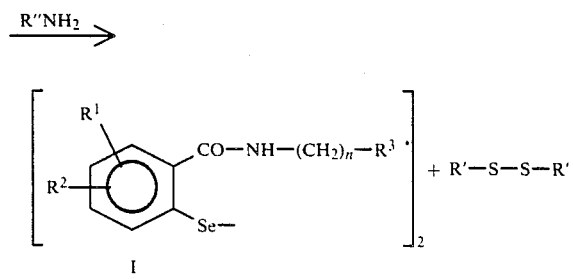

Another process again starts from the benzisoselenazolones of the general formula II. Dissolved in a suitable organic solvent they are reacted at room temperataure with equimolar amounts of a dithiol such as dithioerythrit to yield the compounds of formula I.

The starting benzisoselenazolones of formula II are produced as described in U.S. Pat. No. 4,352,799, DE-OS 3027074, U.S. Pat. No. 4,418,069 and U.S. Pat. No. 4,550,168.

Suitable compounds are for instance:
2-(2-Pyridyl)-1,2-benzisoselenazol-3(2H)-one
2-(3-Pyridyl)-1,2-benzisoselenazol-3(2H)-one
2-(4-Pridyl)-1,2-benzisoselenazol-3(2H)-one
6-Fluoro-2-(2-pyridyl)-1,2-benzisoselenazol-3(2H)-one
6-Chloro-2-(2-pyridyl)-1,2-benzisoselenazol-3(2H)-one
6-Methyl-2-(2-pyridyl)-1,2-benzisoselenazol-3(2H)-one
6-Methoxy-2-(2-pyridyl)-1,2-benzisoselenazol-3(2H)-one
5-Chloro-2-(2-pyridyl)-1,2-benzisoselenazol-3(2H)-one
5-Nitro-2-(2-pyridyl)-1,2-benzisoselenazol-3(2H)-one
7-Methoxy-2-(2-pyridyl)-1,2-benzisoselenazol-3(2H)-one
6,7-Methylendioxy-2-(2-pyridyl)-1,2-benzisoselenazol-3(2H)-one
2-(2-Chloro-3-pyridyl)-1,2-benzisoselenazol-3-(2H)-one
2-(3-Hydroxy-2-pyridyl)-1,2-benzisoselenazol-3(2H)-one
2-(6-Methoxy-3-pyridyl)-1,2-benzisoselenazol-3(2H)-one
2-(3-Nitro-2-pyridyl)-1,2-benzisoselenazol-3(2H)-one
2-(3-Methyl-2-pyridyl)-1,2-benzisoselenazol-3(2H)-one
2-(5-Methyl-2-pyridyl)-1,2-benzisoselenazol-3(2H)-one
2(3,5-Dichloro-2-pyridyl)-1,2-benzisoselenazol-3(2H)-one
2-(4,6-Dimethyl-2-pyridyl)-1,2-benzisoselenazol-3(2H)-one
2-(2-Thiazolyl)-1,2-benzisoselenazol-3(2H)-one
2-(4-Methyl-2-thiazolyl)-1,2-benzisoselenazol-3(2H)-one
2-(5-Nitro-2-thiazolyl)-1,2-benzisoselenazol-3(2H)-one
2-(2-Pyridylmethyl)-1,2-benzisoselenazol-3(2H)-one
2-(3-Pyridylmethyl)-1,2-benzisoselenazol-3(2H)-one
2-(4-Pyridylmethyl)-1,2-benzisoselenazol-3(2H)-one
2-[2-(2-Pyridyl)-ethyl]-1,2.benzisoselenazol-3(2H)-one
2-(2-Thienyl)-1,2-benzisoselenazol-3(2H)-one
2-(2-Piperidinoethyl)-1,2-benzisoselenazol-3(2H)-one
2-(3-Piperidinopropyl)-1,2-benzisoselenazol-3(2H)-one
2-(3-Pyrrolidinopropyl)-1,2-benzisoselenazol-3(2H)-one
2-Furfuryl-1,2-benzisoselenazol-3(2H)-one
2-[2-(2-Furyl)-ethyl]-1,2-benzisoselenazol-3(2H)-one
2-[3-(2-Furyl)-propyl]-1,2-benzisoselenazol-3(2H)-one
2-[4-(2-Furyl)-butyl]-1,2-benzisoselenazol-3(2H)-one
2-[2-(2-Tetrahydrofuryl)-ethyl]-1,2-benzisoselenazol-3(2H)-one
2-(3-Isoxazolyl)-1,2-benzisoselenazol-3(2H)-one
2-[3-(5-Methylisoxazolyl)-1,2-benzisoselenazol-3(2H)-one
2-[2-(Morpholino)-ethyl]-1,2-benzisoselenazol-3(2H)-one
2-[3-(Morpholino)-propyl]-1,2-benzisoselenazol-3(2H)-one.

The present invention is further related to pharmaceutical compounds which comprise a compound of formula I. The pharmaceutical compounds according to the present invention are such that they may be used for enteral as well as oral or rectal and parenteral administration. They contain the pharmaceutical compounds of formula I alone or together with usual, pharmaceutically useful carrier materials. Preferably they are such that they contain the active agent as single dose in accordance to the desired use, for instance as tablets, dragees, capsules, suppositories, granulates, solutions, emulsions or suspensions. The dosage of the active agent usually is between 10 and 1000 mg per day. Preferably between 30 and 300 mg per day. This daily dose may given as a single dose or at several partial doses, preferably in two or three partial doses per day.

The preparation of the compounds according to the present invention is illustrated further in the following examples. The cited melting points have been determined in a Büchi 510-apparatus. They are given in °C. and the data there given are not corrected.

EXAMPLE 1

2,2-Diselenobis-(N-furfuryl-benzamide)

2 g (0.0071 mole) of 2-Furfuryl-1,2-benzisoselenazol-3(2H)-one are dissolved in approximately 50 ml of methanol. There are added to the solution 0.56 ml of ethylmercaptane. The mixture is stirred at room temperature. After 30 minutes, a white compound is precipitated. This precipitate is dissolved in 15 ml of dimethylformamide. 5 ml of a 33% solution of methylamine is added and stirring is continued at room temperature during night. The precipitated white compound is further separated by the addition of ether, is separated by filtration with suction and is dried.

Yield: 1.5 g (74.7% of the theoretical) m.p.: 220° C.

EXAMPLE 2

2,2-Diselenobis-(N-2-pyridyl-benzamide)

This compound is prepared as described in example 1 by reacting:
2 g of 2-(2-Pyridyl)-1,2-benzisoselenazol-3-(2H)-one
0.53 ml of ethylmercaptane
5 ml of 33% methylamine Yield: 1 g (50.2% of the theoretical) m.p.: 105° C.

EXAMPLE 3

2,2-Diselenobis-(N-2-pyridylmethyl-benzamide)

This compound is prepared as described in example 1 by reacting:
1 g of 2-(2-Pyridylmethyl)-1,2-benzisoselenazol-3(2H)-one
0.26 ml of ethylmercaptane
3 ml of 33% methylamine Yield: 0.6 g (60% of the theoretical) m.p.: 192°–196° C.

EXAMPLE 4

2,2-Dieselenobis-(N-2-thienyl-benzamide)

This compound is prepared as described in example 1 by reacting:
2 g of 2-(2-Thienyl)-1,2-benzisoselenazol-3(2H)-one
0.5 ml of ethylmercaptane
5 ml of 33% methylamine Yield: 1 g (50% of the theoretical) m.p.: 225° C.

EXAMPLE 5

2,2-Diselenobis-(N-3-pyridyl-benzamide)

This compound is prepared as described in example 1 by reacting:
2 g of 2-(3-Pyridyl)-1,2-benzisoselenazol-3(2H)-one
0.74 ml of ethylmercaptane
5 ml of 33% methylamine Yield: 1.19 g (36.1% of the theoretical) m.p.: 248° C.

EXAMPLE 6

2,2-Diselenobis-(N-2-thiazolyl-benzamide)

This compound is prepared as described in example 1 by reacting:
2 g of 2-(2-Thiazolyl)-1,2-benzisoselenazol-3(2H)-one
0.5 ml of ethylmercaptane
5 ml of 33% methylamine
Yield: 0.53 g (27.1% of the theoretical) m.p.: 175° C.

EXAMPLE 7

2,2-Diselenobis-[N-3-(5-methylisoxazolyl)-benzamide]

0.5 g (0.00179 mole) of 2-[3-(5-methylisoxazolyl)]-1,2-benzisoselenazol-3(2H)-one are dissolved in 30 ml of methanol. 0.276 g (0.00179 mole) of dithioerythrit are dissolved in 10 ml of methanol and this solution is added to the above methanol solution of the other compound. The mixture is stirred at room temperature for 3 hours and thereafter the solvent is evaporated. The residue is recrystallized from ethanol.
Yield: 0.4 g (34.7% of the theoretical) m.p.: 245° C.

We claim:

1. Diselenobis-benzoic acid amides of the general formula I

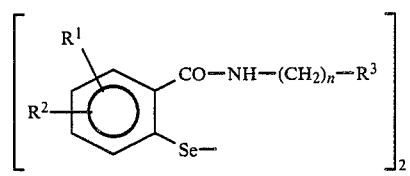

wherein
$R^1$ and $R^2$, which may be the same or different from each other, represent members selected from the group consisting of hydrogen, fluorine, chlorine, methyl, methoxy, nitro and, both together, methylenedioxy and
n is zero or a numeral from 1 to 4 and
$R^3$ is a residue of a member selected from the group consisting of pyridine, thiazole, isoxazole, thiophene and furan, said residue being unsubstituted or substituted once or twice by one or more members selected from the group consisting of chlorine, methyl, methoxy, nitro or hydroxy.

* * * * *